United States Patent
Jung et al.

(10) Patent No.: US 10,842,889 B2
(45) Date of Patent: Nov. 24, 2020

(54) CONTRAST COMPOSITION FOR PHOTOACOUSTIC IMAGING AND METHOD OF PHOTOACOUSTIC IMAGING USING THE SAME

(71) Applicant: SAMSUNG MEDISON CO., LTD., Hongcheon (KR)

(72) Inventors: Jin-woo Jung, Gangwon-do (KR); Deok-woo Choi, Gangwon-do (KR); Jae-ho Lee, Seoul (KR); Won-jae Lee, Seoul (KR); Hyo-keun Lim, Seoul (KR)

(73) Assignee: SAMSUNG MEDISON CO., LTD., Gangwon (KR)

( * ) Notice: Subject to any disclaimer, the term of this patent is extended or adjusted under 35 U.S.C. 154(b) by 404 days.

(21) Appl. No.: 15/171,746

(22) Filed: Jun. 2, 2016

(65) Prior Publication Data
US 2016/0354496 A1 Dec. 8, 2016

(30) Foreign Application Priority Data
Jun. 2, 2015 (KR) .................. 10-2015-0078249

(51) Int. Cl.
*A61K 49/22* (2006.01)
*A61B 5/00* (2006.01)
*A61M 5/00* (2006.01)

(52) U.S. Cl.
CPC ............ *A61K 49/22* (2013.01); *A61B 5/0044* (2013.01); *A61B 5/0095* (2013.01); *A61K 49/226* (2013.01); *A61M 5/007* (2013.01); *A61B 2576/023* (2013.01)

(58) Field of Classification Search
CPC ..... A61K 49/22; A61K 49/226; A61M 5/007; A61B 5/0044; A61B 5/0095; A61B 2576/023
See application file for complete search history.

(56) References Cited

U.S. PATENT DOCUMENTS

| | | | |
|---|---|---|---|
| 5,420,176 A | 5/1995 | Unger et al. | |
| 5,782,771 A * | 7/1998 | Hussman | A61B 5/0084 600/342 |
| 6,699,977 B1 * | 3/2004 | Gerrish | A23L 2/52 424/489 |
| 8,753,608 B2 | 6/2014 | Tabata et al. | |

(Continued)

FOREIGN PATENT DOCUMENTS

| | | |
|---|---|---|
| JP | 2014-031363 A | 2/2014 |
| JP | 2014-129332 A | 7/2014 |

(Continued)

OTHER PUBLICATIONS

Eun D et al: "A Novel Technique for Creating Solid Renal Pseudotumors and Renal Vein-Inferior Vena Caval Pseudothrombus in a Porcine and Cadaveric Model" The Journal of Urology, vol. 180, Oct. 2008, pp. 1510-1514.*

(Continued)

*Primary Examiner* — Bo Joseph Peng
(74) *Attorney, Agent, or Firm* — Morgan, Lewis & Bockius LLP

(57) ABSTRACT

A contrast composition for photoacoustic imaging includes a photoacoustic contrast agent and a gelling agent.

8 Claims, 9 Drawing Sheets

(56) References Cited

U.S. PATENT DOCUMENTS

| | | | |
|---|---|---|---|
| 2005/0163711 A1* | 7/2005 | Nycz | A61K 9/0021 |
| | | | 424/9.1 |
| 2013/0060122 A1* | 3/2013 | Zharov | A61B 5/0059 |
| | | | 600/407 |
| 2014/0017171 A1 | 1/2014 | Tabata et al. | |
| 2014/0271487 A1 | 9/2014 | Fernandes et al. | |
| 2014/0377180 A1 | 12/2014 | Tomatsu et al. | |
| 2015/0023881 A1 | 1/2015 | Kim et al. | |
| 2015/0025373 A1 | 1/2015 | Kim et al. | |
| 2015/0037254 A1 | 2/2015 | Fukui et al. | |
| 2015/0037255 A1 | 2/2015 | Fukui et al. | |
| 2015/0165071 A1 | 6/2015 | Takahashi et al. | |
| 2015/0290345 A1 | 10/2015 | Takahashi et al. | |

FOREIGN PATENT DOCUMENTS

| | | |
|---|---|---|
| JP | 2014-185138 A | 10/2014 |
| JP | 2014-185333 A | 10/2014 |
| WO | 2011/006263 A1 | 1/2011 |
| WO | 2014/129674 A1 | 8/2014 |
| WO | 2015/000058 A1 | 1/2015 |
| WO | 2015/012540 A1 | 1/2015 |

OTHER PUBLICATIONS

Pan et al, A Brief Account of Nanoparticle Contrast Agent for Photoacoustic Imaging, Wiley Interdiscip Rev Nanomed Nanobiotechnol (Year: 2013).*

Sheinfeld et al ,Photoacoustic Doppler measurement of flow using tone burst excitation, Optics Express vol. 18, No. 5, pp. 4212-4221 (Year: 2010).*

Bond et al, Light Absorption by Carbonaceous particles, Aerosol Science and Technology, vol. 40, pp. 27-67 (Year: 2006).*

J. Davies, et al., "Methylene Blue But Not Indigo Carmine Causes DNA Damage to Colonocytes In Vitro and In Vivo at Concentrations Used in Clinical Chromoendoscopy", PostScrip, pp. 155-156.

Mahadevan et al., "Methylene Blue But Not Indigo Carmine is Toxic to Human Luteal Cells In Vitro", Reproductive Toxicology, vol. 7, No. 6, (1993), pp. 631-633.

Yan Lu et al, "Methylene Blue-Mediated Photodynamic Therapy Induces Mitochondria-Dependent Apoptosis in Hela Cell", Journal of Cellular Biochemistry, 105:1451-1460 (2008).

Kuk-Youn Ju et al., "Bio-Inspired, Melanin-Like Nanoparticles as a Highly Efficient Contrast Agent for T 1-Weighted Magnetic Resonance Imaging", Biomacromolecules 2013, 14:3491-3497.

Cui-Yun Yu et al., "In vitro and in vivo evaluation of pectin-based nanoparticles for hepatocellular carcinoma drug chemotherapy", Mol. Pharm. 2014;11:638-44.

Minghua Xu et al., "Photoacoustic imaging in biomedicine", Review of Scientific Instruments 77, pp. 041101-041101-22 (2006).

Xueding Wang et al., "Noninvasive laser-induced photoacoustic tomography for structural and functional in vivo imaging of the brain", Nat Biotechnol 2003;21:803-806.

Xueding Wang et al., "Noninvasive photoacoustic tomography of human peripheral joints toward diagnosis of inflammatory arthritis", Opt Left 2007;32:3002-3004.

S. Manohar et al., "The twente photoacoustic mammoscope: system overview and performance", Phys Med Biol 2005;50:2543-2557.

J-T Oh, et al., "Three-dimensional imaging of skin melanoma in vivo by dual-wavelength photoacoustic microscopy," J . Biomed Opt 2006;11:34032.

S. Yang et al., "Functional imaging of cerebrovascular activities in small animals using high-resolution photoacoustic tomography", Med Phys 2007;34:3294-3301.

C. Li et al., "Photoacoustic tomography and sensing in biomedicine", Phys. Med. Bio. 2009;54:59-97.

Yu Wang et al., "In vivo three-dimensional photoacoustic imaging based on a clinical matrix array ultrasound prob", J Biomed Opt 2012;17:061208.

Minghua Xu et al., "Universal back-projection algorithm for photoacoustic computed tomography", Phys Rev E Stat Nonlin Soft Matter Phys 2005;71:016706.

S. Park et al., "Beamforming for photoacoustic imaging using linear array transducer", IEEE ultrasonics Symposium 2007;856-859.

R. G. Sturmey et al., "Removal of red light minimizes methylene blue-stimulated DNA damage in oesophageal cells: implications for chromoendoscopy", Mutagenesis 2009;24:253-258.

J.R. Olliver et al., "Chromoendoscopy with methylene blue and associated DNA damage in Barrett's oesophagus", Lancet 2003;362:373-4.

K. Ju et al., "Bio-inspired, melanin-like nanoparticles as a highly efficient contrast agent for T1-weighted magnetic resonance imaging", Biomacromolecules 2013;14:3491-3497.

Insoluble Dietary Fiber, Chapter 2, with English translation.

T.N. Erpelding, et al., "Sentinel Lymph Nodes in the Rat: Noninvasive Photoacoustic and US Imaging with a Clinical US System", Radiology, vol. 256, No. 1, Jul. 2010, pp. 102-110.

Y. Sun et al., "Quantitative three-dimensional photoacoustic tomography of the finger joint: an in vivo study", J. Biomed. Opt., (2009), 14(6).

X. Wang et al., "Noninvasive imaging of hemoglobin concentration and oxygenation in the rat brain using high-resolution photoacoustic tomography", J. Biomed. Opt. (Mar./Apr. 2006) 11(2), pp. 024015-1 through 024015-9.

Extended European Search Report issued in Application No. 15194666.2 dated Oct. 20, 2016.

* cited by examiner

WEEK 1

WEEK 2

WEEK 3

WEEK 4

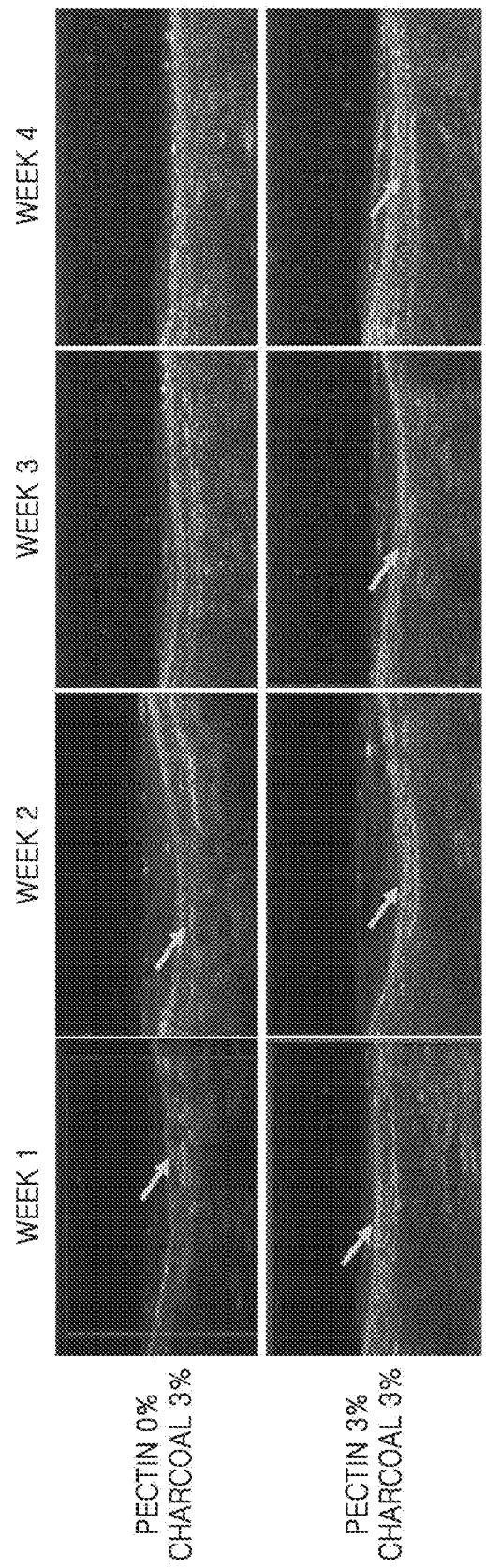

CONTRAST COMPOSITION FOR PHOTOACOUSTIC IMAGING AND METHOD OF PHOTOACOUSTIC IMAGING USING THE SAME

CROSS-REFERENCE TO RELATED APPLICATION

This application claims the benefit of Korean Patent Application No. 10-2015-0078249, filed on Jun. 2, 2015, in the Korean Intellectual Property Office, the disclosure of which is incorporated herein in its entirety by reference.

BACKGROUND

1. Field

One or more exemplary embodiments relate to a contrast composition for photoacoustic imaging and a method of photoacoustic imaging using the contrast composition.

2. Description of the Related Art

Photoacoustic imaging is a hybrid imaging technique for noninvasively obtaining images of biological tissues using a photoacoustic effect, and studies on the photoacoustic imaging have been conducted actively in recent years.

The photoacoustic effect refers to a phenomenon in which a material absorbs energy in the form of light or radio waves and thermally expands to generate an acoustic wave. In this regard, when short pulses of light, such as laser pulses, are irradiated to the biological tissues, the energy absorbed in the tissues is converted into heat, which causes thermoelastic expansion. Then, signals having an ultrasound wave frequency range of several MHz to several tens of MHz are generated, and the signals may be received by using an ultrasound wave probe. When the ultrasound wave signals received by the probe are converted by employing various algorithms, a photoacoustic image may be produced.

Although contrast agents such as methylene blue or indigo carmine have been used as a photoacoustic contrast agent in recent years, the contrast agents disappear due to being absorbed by the body within a certain period of time after the injection. Therefore, there is a demand for an injection type contrast agent that may continuously remain in the body by using a material capable of generating a photoacoustic signal.

SUMMARY

One or more exemplary embodiments include a contrast composition for photoacoustic imaging, the composition including a photoacoustic contrast agent and a gelling agent.

One or more exemplary embodiments include a method of photoacoustic imaging by using a contrast composition for photoacoustic imaging, the composition including a photoacoustic contrast agent and a gelling agent.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings in which:

FIG. 5 shows photoacoustic images of a contrast agent including pectin and charcoal and a charcoal contrast agent not including pectin in a liver, captured 1 week to 4 weeks after injection.

DETAILED DESCRIPTION

Figure 1A:
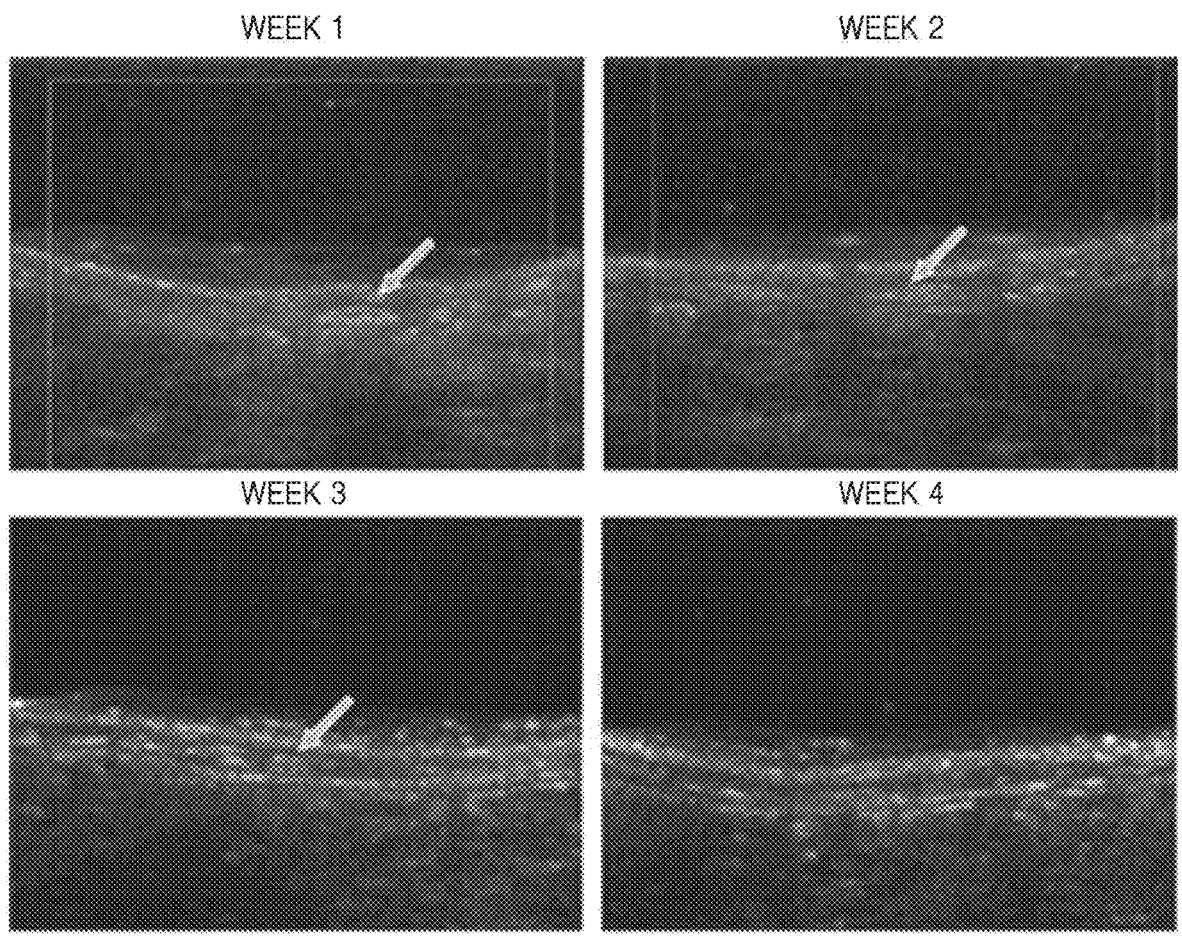
FIG. 1A shows photoacoustic images of a melanin contrast agent not including pectin in a liver, captured 1 week to 4 weeks after injection.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an exemplary embodiment, provided are a contrast composition for photoacoustic imaging, the composition including a photoacoustic contrast agent and a gelling agent.

According to another embodiment, provided are a contrast composition for use in photoacoustic imaging, the composition including a photoacoustic contrast agent and a gelling agent.

As used herein, the term "photoacoustic" refers to a phenomenon in which acoustic waves are propagated as the result of a local temperature increase and thermal expansion when a material absorbs light. A photoacoustic effect may be measured by detecting a small amount of light absorption at a high sensitivity and may be measured in a sample, where photoacoustic waves from the sample may not be measured by using a general optical technique, and thus the photoacoustic effect may be used in a measurement using spectroscopy.

Also, as used herein, the term "photoacoustic imaging" denotes a series of processes which include injecting a photoacoustic contrast agent to a site subjected to the imaging, irradiating light, e.g., laser pulses, to the site, inducing generation of ultrasound waves of a wideband (e.g., MHz) to the contrast agent due to energy transferred by the laser pulses, and detecting the ultrasound waves thus generated by using an ultrasound probe to form an image.

Also, as used herein, the term "photoacoustic contrast agent" may refer to a material having the photoacoustic effect or may include a hybrid biomedical imaging modality contrast agent that is developed based on the photoacoustic effect. The photoacoustic contrast agent may be a light absorptive dye material, and examples of the photoacoustic contrast agent may include melanin, charcoal, methylene blue, indigo carmine, indocyanine green, evans blue, azure blue, brilliant blue, nile blue, or a combination thereof. The photoacoustic contrast agent is commercially available or may be synthesized or prepared by using a method known to a person or ordinary skill in the art. For example, melanins are a biopolymer that are found in various parts of living organisms such as plants, animals, and protista, and are usually categorized into black-brown eumelanin and yellow-reddish pheomelanin. Eumelanins are derived from 3,4-dihydroxy-L-phenylalanine(L-DOPA) or 2-(3,4-dihydroxyphenyl)ethylamine (dopamine). Pheomelanins are derived from L-DOPA or dopamine in the presence of mercapto group (—SH)-containing compounds such as cysteine, glutathione, etc. Melanins may be collected from natural sources. For example, melanin may be extracted from squid ink. Also, melanin may be synthesized by using dopamine or a melanin precursor of DOPA or cysteine. For example, melanin may be prepared by polymerization while oxidizing dopamine that is produced by a chemical reaction between a dopamine H+X− containing aqueous solution (where, "H+X−" is an acid) and a base. Melanin, as a pigment molecule that absorbs a large amount of light, has biocompatibility in terms of medical imaging which is safe when administered in the body of a subject and has a good photoacoustic effect.

An amount of the photoacoustic contrast agent may be in a range of about 0.5 wt % to about 15 wt % based on the total weight of the contrast composition. In terms of light absorbing ability, the contrast composition may include the photoacoustic contrast agent at an amount, for example, in a range of about 0.5 wt % to about 10 wt %, about 1 wt % to about 10 wt %, about 3 wt % to about 10 wt %, or about 3 wt % to about 5 wt %, or, for example, at about 2 wt %, about 3 wt %, about 4 wt %, or about 5 wt %.

Also, the photoacoustic contrast agent is a light absorptive dye material which may absorb incident light having a wavelength in a range of about 500 nm to about 1,300 nm. For example, a range of the wavelength of the incident light may be about 500 nm to about 1,000 nm, about 600 nm to about 1,000 nm, or about 600 nm to about 700 nm. A frequency range of the acoustic waves generated when the photoacoustic contrast agent absorbs light may be, for example, about 1 MHz to about 50 MHz, about 1 MHz to about 40 MHz, about 1 MHz to about 30 MHz, about 2 MHz to about 20 MHz, or about 2 MHz to about 10 MHz. The acoustic waves generated by the photoacoustic contrast agent may be detected by using, for example, an ultrasound wave scanner.

As used herein, the term "gelling agent" may refer to a material having an ability to form gel and a viscosity of a certain level or higher. An example of the gelling agent may be hydrocolloid, and examples of hydrocolloid may include polysaccharides and proteins. Examples of polysaccharides may include natural gum, artificial gum, natural seaweed extract, natural seed gum, natural plant extract, and natural fruit extract. More particularly, polysaccharide may be at least one selected from pectin, amylo pectin, agar, arabic gum, tragacanth gum, karaya gum, locust bean gum, xanthan gum, guar gum, tara gum, tamarind gum, psyllium gum, ghatti gum, carrageenan, alginate, agarose, puselran, dextran, starch, curdlan, and a combination thereof. Also, protein may be at least one selected from gelatin, soybean protein, egg protein, fish-flesh protein, and a combination thereof. The gelling agent is commercially available or may be synthesized or prepared by using a method known to a person of ordinary skill in the art. For example, when pectin is dissolved in an aqueous solution, gel may be formed, and the gel may include D-galacturonic acid as a basic constituent unit and has a linear structure including a plurality of the constituent units that are connected via α-1,4 bonds. Pectin may be obtained through purification by using citrus unshiu peel or apple pomace as a raw material. The gelling agent including pectin is safe when administered into the body of a subject and gives a viscosity to the contrast composition, and thus the gelling agent may function as a viscous medium that delays absorption of the contrast composition into tissues or blood vessels.

An amount of the gelling agent may be, for example, in a range of about 0.5 wt % to about 15 wt % based on the total weight of the contrast composition. In terms of a viscosity of the gelling agent, the contrast composition may include the gelling agent at an amount, for example, in a range of about 0.5 wt % to about 10 wt %, about 1 wt % to about 10 wt %, about 1.5 wt % to about 10 wt %, or about 2 wt % to about 5 wt %, or, for example, at about 1.5 wt %, about 2 wt %, about 3 wt %, or about 4 wt %. Also, a viscosity of the gelling agent may be about 50 cP or higher. The viscosity may be measured at a temperature of about 20° C., and the viscosity of the gelling agent may be, for example, in a range of about 50 cP to about 400 cP, about 100 cP to about 350 cP, about 100 cP to about 300 cP, about 150 cP to about 300 cP, or about 200 cP to about 300 cP.

In one exemplary embodiment, the contrast composition may be used to diagnose whether a subject has a disease or not. In another exemplary embodiment, the contrast composition may be injected into tissues or blood vessels. In another exemplary embodiment, the contrast composition may have durability in an injection site. Through diagnostic imaging of an arbitrary anatomical structure, the contrast composition may be used in diagnosis of finding out whether a disease is present in the site of the imaging or not. Diagnosis of the presence of a disease may include checking prognosis, development, or treatment of the diagnosed disease as well as confirming the presence of an initially found disease at an early stage of examination. For example, the contrast composition according to an exemplary embodiment has durability in an injection site, and such durability of the contrast composition allows finding a location of cancer when a size of a lesion decreases or the lesion becomes invisible after anticancer treatment of bathypelagic cancer such as liver cancer without a surgical operation. The durability may indicate an increase intensity of light for photoacoustic imaging or an increase period of the total time for detecting a contrast effect. A period of the total time for detecting the photoacoustic image may be at least a week, for example, about 2 weeks, 3 weeks, 4 weeks, 5 weeks, or 6 weeks or more. Examples of the disease may vary depending on the site subjected to be imaged and may include cancers such as breast cancer, gastrointestinal diseases such as inflammatory bowel disease, cerebrovascular disease, cardiovascular disease, vascular diseases such as peripheral vascular disease, inflammatory diseases such as arthritis or pancreatitis, urinary tract diseases, or eye diseases.

A dosage of administration of the contrast composition according to an exemplary embodiment may be administered through various administration pathways. Examples of the administration pathways may include oral, sublingual, parenteral (e.g., subcutaneous, intramuscular, intraarterial, intraperitoneal, intrathecal, or intravenous), rectal, and topical (including transdermal) pathways, inhalation, and injection, or insertion of an implant device or a substance. For example, the contrast composition according to an exemplary embodiment may be administered in tissue or blood vessels of the subject. The administration may be performed by using a vial or a syringe including a dose of a suitable administration preparation or, for example, a material needed for the desired diagnosis or contrast effect, once or several times. The preparation or the material may be administered for about 5 seconds to about 20 minutes, or, for example, about 15 seconds to about 5 minutes each time. As used herein, the terms "dosage" and "dose" may refer to an amount of a material of one administration needed for the desired diagnosis or contrast effect. For example, the dose may be in a range of about 0.025 mg/kg to 10,000 mg/kg of body weight, about 0.05 mg/kg to 5,000 mg/kg of body weight, about 0.1 mg/kg to 1,000 mg/kg of body weight, about 0.5 mg/kg to 500 mg/kg of body weight, or about 1 mg/kg to 250 mg/kg of body weight, Examples of an animal that may be subjected to the treatment according to an exemplary embodiment may include a human or other mammalian subject, for example, a monkey, a mouse, a rat, a rabbit, a sheep, a cow, a dog, a horse, or a pig.

According to another exemplary embodiment, provided is a method of photoacoustic imaging by using a contrast composition for photoacoustic imaging, the composition including a photoacoustic contrast agent and a gelling age.

The method may include administrating the contrast composition for photoacoustic imaging to a subject.

Also, the method may include irradiating light to a site of the subject where the contrast composition for photoacoustic imaging is administered to generate acoustic waves; and detecting the acoustic waves to form an image.

The contrast composition, the subject, the pathways of injecting the contrast composition in the subject, the preparation, and the dosage in the present exemplary embodiment are the same as defined above.

The irradiating of light may include applying light energy into the contrast composition, or, for example, irradiating laser pulses to the contrast composition. A wavelength of the irradiated light may be in a range of about 500 nm to about 1,000 nm, about 600 nm to about 1,000 nm, or about 600 nm to about 700 nm.

The site of the subject may include a region that may be a target of the diagnosis or that may be subjected to the imaging. The site to be a target or subjected to the imaging may refer to a site to which the medication needs to be delivered or an image of which is needed. The site of the subject may be, for example, a region where a lesion is present, an abdominal cavity, a heart, a gastrointestinal tract, a pancreas, a gall bladder, a spleen, lymph nodes, a liver, a kidney, or an eye. The region where a lesion is present may include a site where a disease is found, a site potentially having a disease, or a site where a disease was once previously found, and the disease is the same as described above.

When light is irradiated to the subject, the site of the subject or the contrast composition absorbs the light and converts the light into heat to cause thermoelastic expansion, and thus propagation of acoustic waves may be induced. The acoustic waves may be ultrasound waves having a frequency range of about 1 MHz to about 50 MHz, about 1 MHz to about 40 MHz, about 1 MHz to about 30 MHz, about 2 MHz to about 20 MHz, or about 2 MHz to about 10 MHz.

The detecting of the acoustic waves to form an image may be performed through an ultrasound wave system. The ultrasound wave system may include an ultrasound wave detector, and an example of the device may be an ultrasound wave detector including a transducer. The transducer interconverts energy of an electric signal and an ultrasound wave signal to detect the acoustic waves, and thus an image may be formed in this regard.

Thereinafter, one or more exemplary embodiments will be described in detail with reference to the following examples. However, these examples are not intended to limit the scope of the one or more exemplary embodiments.

EXAMPLE

Photoacoustic Contrast Effect Analysis of Durable Injection-type Mixture Contrast Agent 1. Preparation of Mixture Contrast Agent 4 compositions were prepared to formulate a contrast agent of a durable injection type.

In particular, a mixture for photoacoustic imaging included a dye material that would serve as a contrast agent and a viscous medium that would facilitate absorption of the mixture into tissues. The dye material included melanin extracted from squid (Sepia officinalis) (available from Sigma-Aldrich, St. Louis, Mo., USA) and charcoal (Activated charcoal) (available from Sigma-Aldrich, St. Louis, Mo., USA). The viscous medium was pectin extracted from citrus peel (Sigma-Aldrich, St. Louis, Mo., USA). Here, the melanin and the charcoal were dissolved in deionized water at a concentration of 3%, and the pectin was dissolved at a concentration of about 2% to about 3%. Also, a contrast agent only including the melanin and charcoal at a concentration of 3% was prepared as a control group.

2. Durability Analysis of Mixed Contrast Agent

In order to test durability of the 4 samples prepared in Example 1 in the body, the samples were injected into a liver and a subcutaneous muscle layer of a rat and then quantitatively and qualitatively analyzed by photoacoustic imaging upto 4 weeks.

In particular, the rat was a Spraque-Dawley rat having a body weight of about 350 g, more or less. A control group was divided into a group using 3% melanin or charcoal only, a group using a pectin-melanin mixture including 2% pectin, and a group using a pectin-charcoal mixture to confirm whether pectin has a delaying effect. Then, each of the experimental groups was divided into smaller groups having the injection in a subcutaneous muscle layer or two organs of the liver, and thus a delaying effect from the two organs having a difference in a blood flow rate was confirmed. Each of the small groups had 10 rats. A subcutaneous muscle layer injection of the contrast agent was performed by giving an anesthetic to the rat and injecting about 50 uL of the contrast agent to a thigh muscle layer to a depth of about 3 nm to about 5 nm from the skin by using a syringe (1 mL/24 G). A liver injection of the contrast agent was performed by giving an anesthetic to the rat, cutting the abdomen of the rat, and injecting about 50 uL of the contrast agent into the parenchyma to a depth of 2 mm from a surface of the liver.

An instrument for detecting ultrasound waves was a clinical instrument added with a data process device and a laser control facility on Accuvix A30 (Samsung Medison, Seoul, Korea). A linear probe transducer for detecting ultrasonic waves was L5-13/50 (Samsung Medison, Seoul, Korea) of a linear array type having a center frequency of 8.5 MHz and 256 diodes, and thus ultrasonic wave imaging and photoacoustic imaging signals were sequentially detected by all the 256 diodes. A laser equipment for generating photoacoustic signals was a product that supplies a light source of a pulse type by using a Q-switching technique with Phocusmobile (Opotek, USA) that uses an Nd:YAG laser. Conditions of using the equipment included a wavelength of 700 nm, an output of 60 mJ, and a repetition rate of 5 Hz to increase light absorbance of melanin. The laser beam thus generated was focused on optic fiber bundle through an optical lens and then divided into two so that each end of the lasers from a light-emitting part was located next to both sides of the ultrasonic wave probe, and thus an output direction of the laser matched a scanning direction of the ultrasonic wave probe.

The photoacoustic image was taken every week for 4 weeks after injecting the contrast agent to a subject animal. While the photoacoustic image was taken, the subject animal's anesthesia state was maintained, and an abdomen of the animal faced upward to obtain images of a subcutaneous muscle layer of a liver and a leg. The ultrasonic wave probe and the light-emitting part of the laser were equipped in a control device, and thus the images were taken while moving the rat in X-Y-Z axis with a reference to a sagittal plane. Then, a laser was irradiated to qualitatively and quantitatively analyze the photoacoustic signals transmitted from the injected contrast agent.

The qualitative analysis was performed by evaluating whether the photoacoustic signals generated from the contrast agent were detected or not, and the results of using melanin as the dye material are shown in FIGS. 1A to 4A. Also, the results of using charcoal that is used in tattooing for detecting breast cancer are shown in FIG. 5.

The quantitative analysis was performed by saving the photoacoustic signals, calculating relative numerical values by using MATLAB (Mathworks, Natick, USA), and using melanin as a dye material. The results of the quantitative analysis are shown in FIGS. 1B to 4B and Tables 1 to 4.

TABLE 1

Average values of photoacoustic signals obtained after injecting melanin to a liver

| No. | Week 1 | Week 2 | Week 3 | Week 4 |
|---|---|---|---|---|
| 1 | 244.0 | 190.4 | 119.6 | 103.2 |
| 2 | 238.0 | 196.8 | 148.1 | 109.7 |
| 3 | 250.1 | 201.5 | 160.4 | 115.8 |
| 4 | 249.5 | 215.6 | 168.2 | 125.6 |
| 5 | 239.9 | 210.6 | 156.6 | 119.5 |
| 6 | 241.6 | 220.5 | 164.5 | 123.9 |
| 7 | 236.4 | 199.6 | 128.3 | 101.6 |
| 8 | 249.7 | 201.3 | 136.5 | 106.4 |
| 9 | 236.9 | 189.6 | 113.6 | 98.6 |
| 10 | 244.6 | 199.6 | 129.5 | 101.7 |
| Average | 243.1 | 202.5 | 142.5 | 110.6 |

TABLE 2

Average values of photoacoustic signals obtained after injecting a mixture of pectin and melanin to a liver

| No. | Week 1 | Week 2 | Week 3 | Week 4 |
|---|---|---|---|---|
| 1 | 245.7 | 240.9 | 247.9 | 240.3 |
| 2 | 250.6 | 234.5 | 247.0 | 242.7 |
| 3 | 249.6 | 242.3 | 251.6 | 239.3 |
| 4 | 251.2 | 246.5 | 240.6 | 243.4 |
| 5 | 243.2 | 239.4 | 241.7 | 243.1 |
| 6 | 246.4 | 236.9 | 240.6 | 241.3 |
| 7 | 248.3 | 239.4 | 226.8 | 236.3 |
| 8 | 253.8 | 243.1 | 247.6 | 235.3 |
| 9 | 236.2 | 233.6 | 238.4 | 232.4 |
| 10 | 251.1 | 252.7 | 246.8 | 239.2 |
| Average | 247.6 | 240.9 | 242.9 | 239.3 |

TABLE 3

Average values of photoacoustic signals obtained after injecting melanin to a subcutaneous muscle layer

| No. | Week 1 | Week 2 | Week 3 | Week 4 |
|---|---|---|---|---|
| 1 | 238.5 | 242.1 | 237.5 | 230.9 |
| 2 | 242.8 | 237.2 | 233.7 | 221.7 |
| 3 | 244.3 | 239.7 | 241.1 | 237.6 |
| 4 | 243.7 | 243.1 | 234.7 | 229.2 |
| 5 | 244.6 | 237.9 | 231.4 | 238.4 |
| 6 | 241.9 | 238.3 | 236.2 | 231.7 |
| 7 | 242.7 | 234.7 | 232.7 | 238.2 |
| 8 | 250.8 | 246.7 | 234.3 | 239.5 |
| 9 | 241.4 | 238.4 | 237.3 | 234.3 |
| 10 | 239.3 | 245.8 | 241.2 | 246.7 |
| Average | 243.0 | 240.4 | 236.0 | 234.8 |

TABLE 4

Average values of photoacoustic signals obtained after injecting a mixture of pectin and melanin to a subcutaneous muscle layer

| No. | Week 1 | Week 2 | Week 3 | Week 4 |
|---|---|---|---|---|
| 1 | 252.2 | 253.9 | 249.0 | 251.4 |
| 2 | 245.8 | 251.7 | 246.9 | 248.6 |
| 3 | 248.1 | 246.9 | 249.6 | 246.9 |
| 4 | 250.4 | 249.7 | 246.2 | 248.5 |
| 5 | 252.6 | 250.7 | 244.7 | 251.4 |
| 6 | 243.7 | 251.2 | 253.4 | 248.4 |
| 7 | 251.2 | 249.4 | 239.4 | 244.6 |
| 8 | 254.3 | 251.4 | 248.3 | 253.2 |
| 9 | 244.1 | 246.4 | 242.3 | 249.3 |
| 10 | 253.8 | 251.3 | 247.8 | 251.4 |
| Average | 249.6 | 250.2 | 246.7 | 249.4 |

Figure 1B:
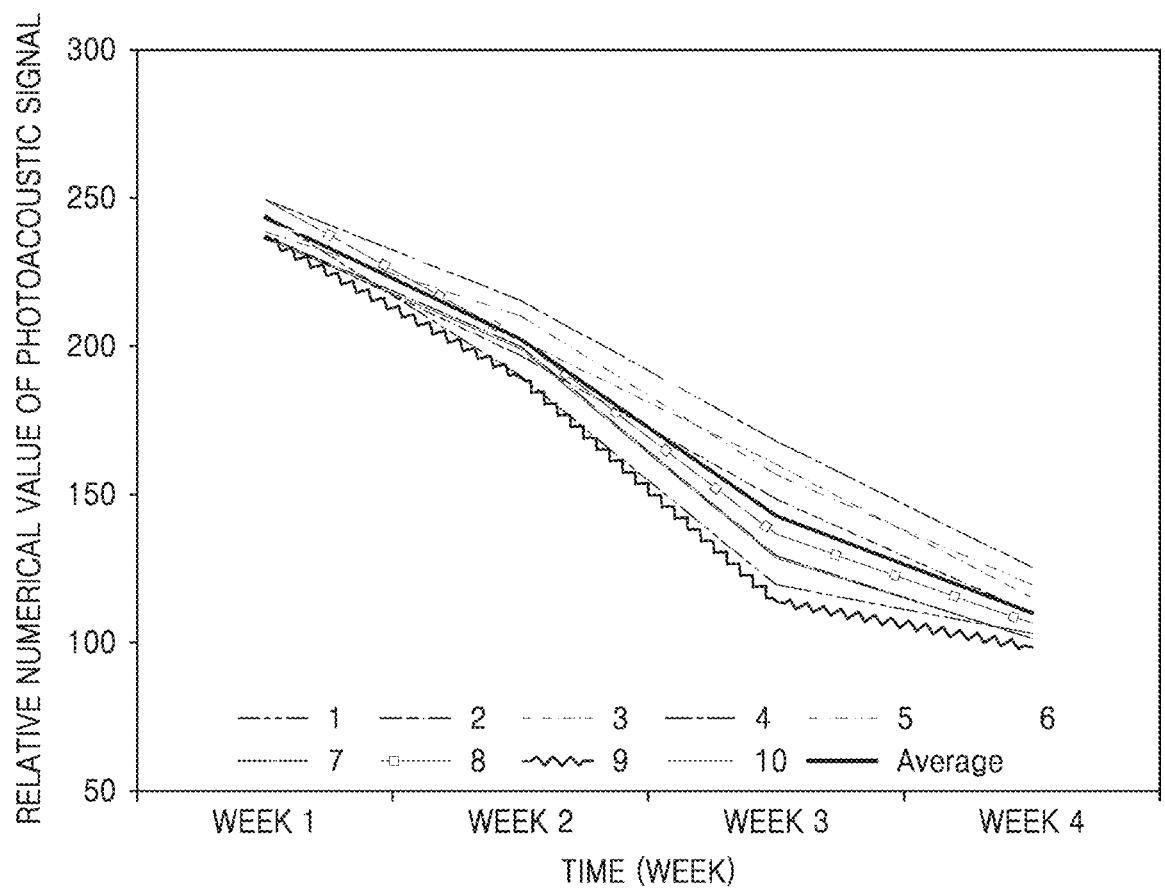
FIG. 1B is a graph of the photoacoustic images of a melanin contrast agent not including pectin in a liver, captured 1 week to 4 weeks after injection.

FIGS. 1A and 1B show photoacoustic images of a melanin contrast agent not including pectin in a liver captured 1 week to 4 weeks after injection and relative numerical values of photoacoustic signals obtained therefrom.

Figure 2A:
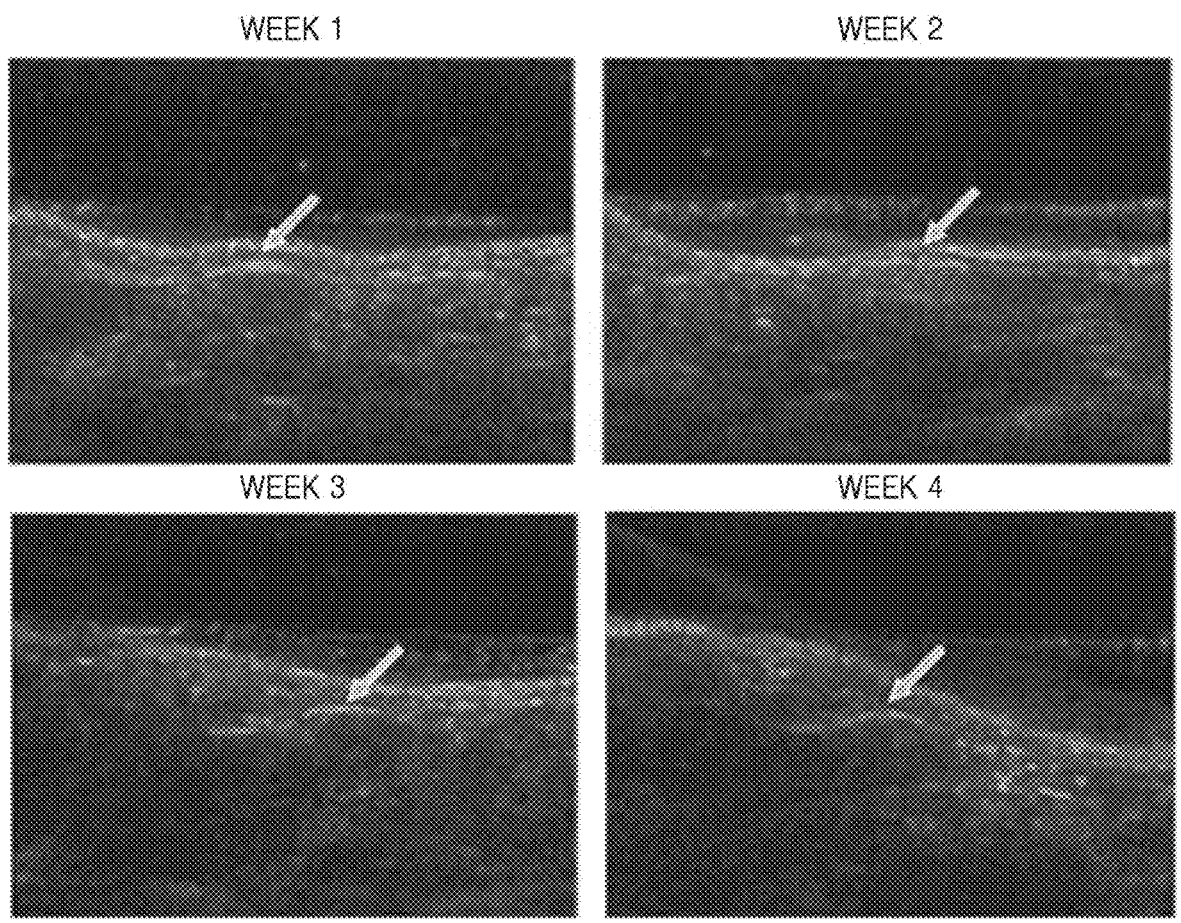
FIG. 2A shows photoacoustic images of a contrast agent including pectin and melanin in a liver, captured 1 week to 4 weeks after injection, according to an exemplary embodiment.
Figure 2B:
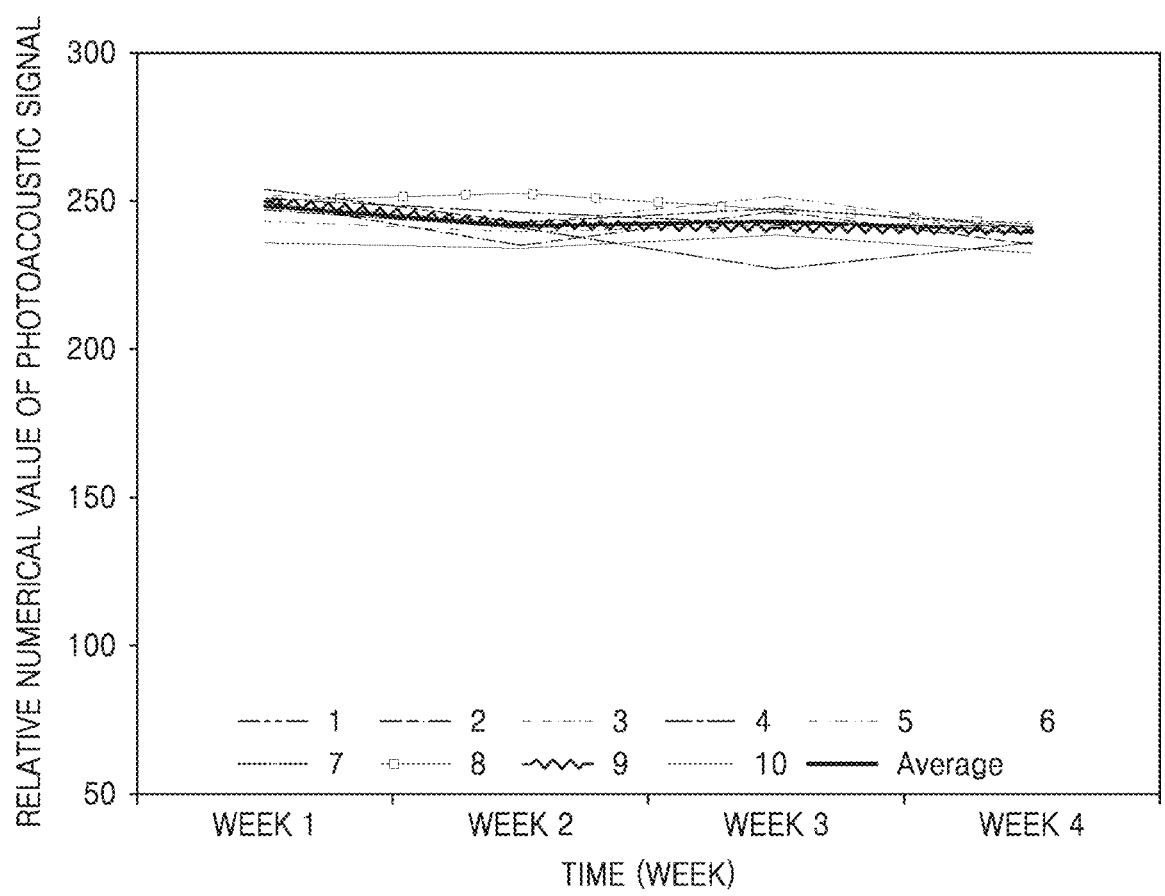
FIG. 2B is a graph quantitatively illustrating the photoacoustic images of a contrast agent including pectin and melanin in a liver, captured 1 week to 4 weeks after injection, according to an exemplary embodiment.

FIGS. 2A and 2B show photoacoustic images of a contrast agent including pectin and melanin in a liver captured 1 week to 4 weeks after injection according to an exemplary embodiment and relative numerical values of photoacoustic signals obtained therefrom.

Figure 3A:
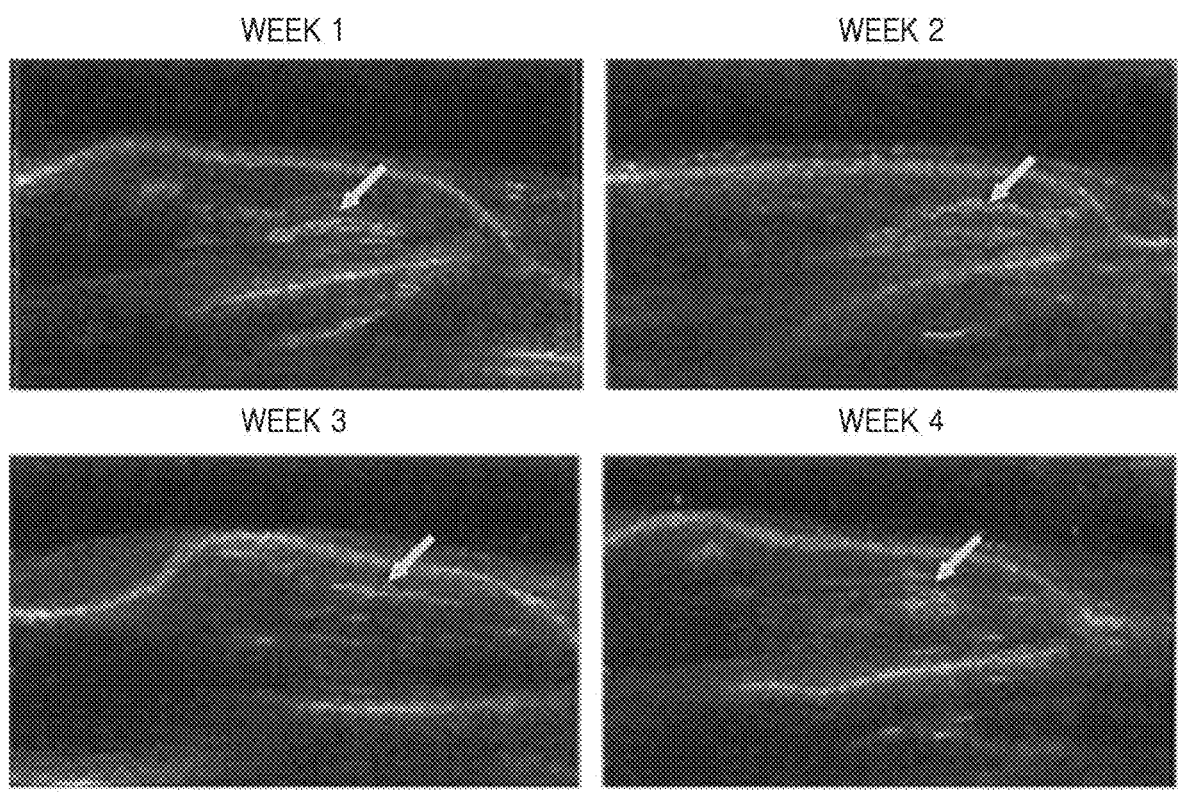
FIG. 3A shows photoacoustic images of a melanin contrast agent not including pectin in a subcutaneous muscle layer, captured 1 week to 4 weeks after injection.
Figure 3B:
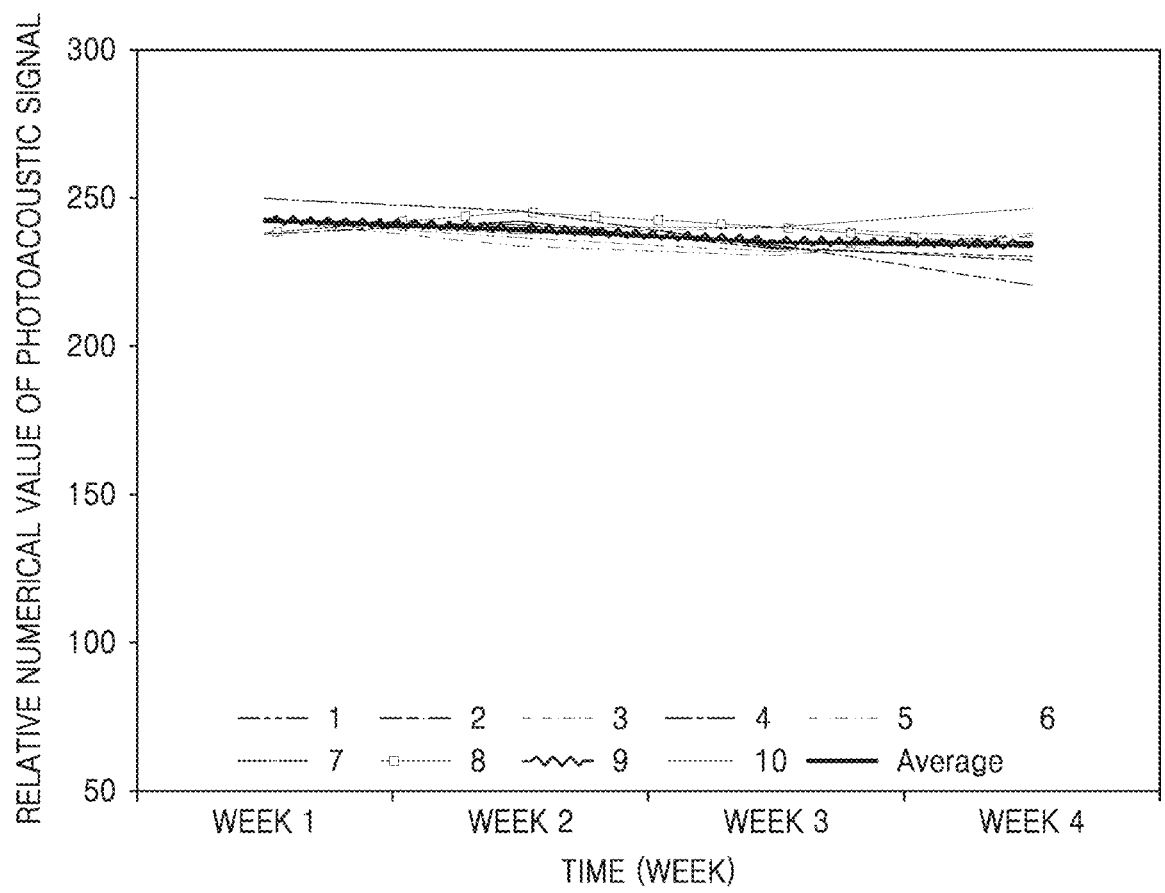
FIG. 3B is a graph quantitatively illustrating the photoacoustic images of the melanin contrast agent not including pectin in a subcutaneous muscle layer, captured 1 week to 4 weeks after injection.

FIGS. 3A and 3B show photoacoustic images of a melanin contrast agent not including pectin in a subcutaneous muscle layer captured 1 week to 4 weeks after injection and relative numerical values of photoacoustic signals obtained therefrom.

Figure 4A:
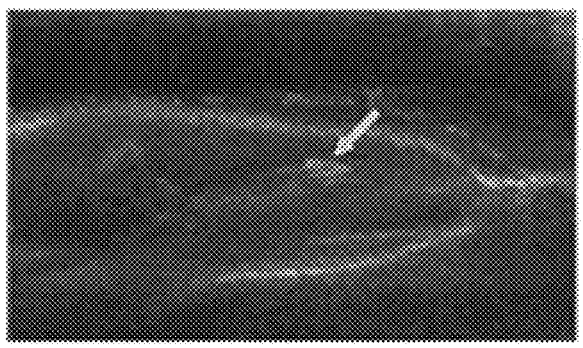
FIG. 4A shows photoacoustic images of a melanin contrast agent including pectin and melanin in a subcutaneous muscle layer, captured 1 week to 4 weeks after injection.
Figure 4A:
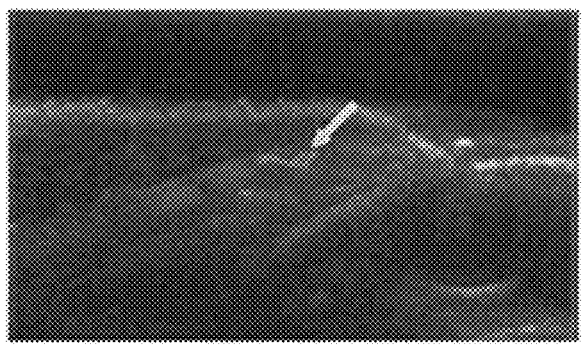
Figure 4A:
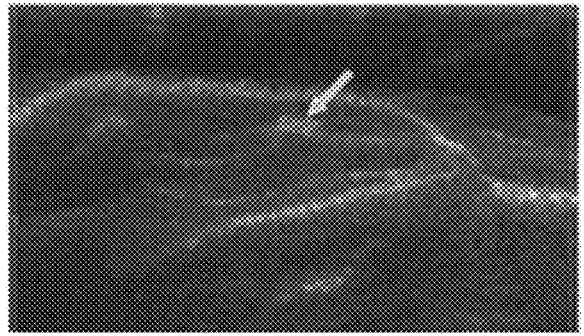
Figure 4A:
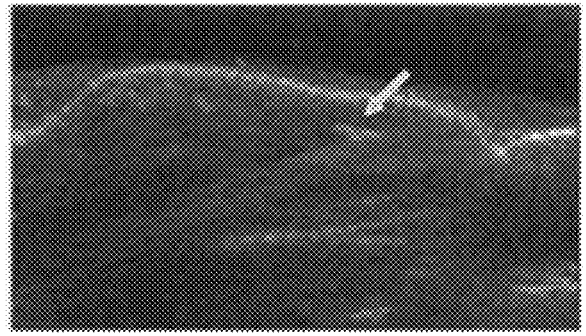
Figure 4B:
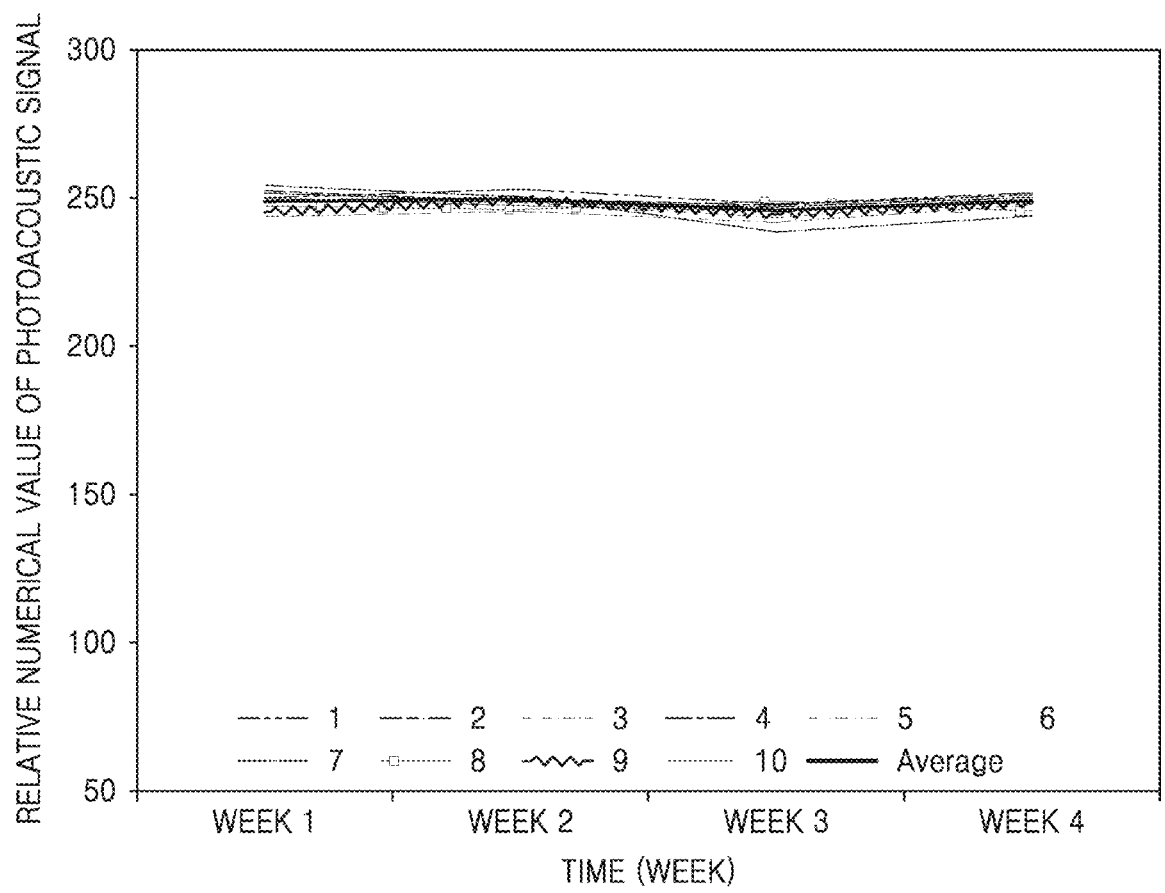
FIG. 4B is a graph quantitatively illustrating the photoacoustic images of a melanin contrast agent including pectin and melanin in a subcutaneous muscle layer, captured 1 week to 4 weeks after injection.

FIGS. 4A and 4B show photoacoustic images of a melanin contrast agent including pectin and melanin in a subcutaneous muscle layer captured 1 week to 4 weeks after injection and relative numerical values of photoacoustic signals obtained therefrom.

FIG. 5 shows photoacoustic images of a contrast agent including pectin and charcoal and a charcoal contrast agent not including pectin in a liver, captured after 1 week to 4 weeks after injection.

As shown in FIGS. 1A and 1B and Table 1, it may be confirmed that the photoacoustic signals continuously decreased over the 4 weeks when only melanin was injected to the liver, and the photoacoustic signals was not detected in week 4. Meanwhile, as shown in FIGS. 2A and 2B and Table 2, despite of a number of blood vessels in the liver, the photoacoustic signals were continuously observed until week 4 when a mixed contrast agent of pectin and melanin was injected to the liver.

As shown in FIGS. 3A and 3B and Table 3, it may be confirmed that the photoacoustic signals continuously decreased over the 4 weeks when only melanin was injected to the subcutaneous muscle layer. Meanwhile, as shown in FIGS. 4A and 4B and Table 4, intensities of the photoacoustic signals were not decreased until week 4 when a mixed contrast agent of pectin and melanin was injected to the subcutaneous muscle layer, where a relatively less number of blood vessels exist in the subcutaneous muscle layer.

Also, as shown in FIG. 5, the charcoal used in a tattooing technique for detecting breast cancer may be detected by photoacoustic imaging, and, when a material having viscosity is mixed with the charcoal according to an embodiment, it may be confirmed that intensities of the photoacoustic signals were not decreased until week 4.

In this regard, it may be known that when a material having viscosity is mixed with the photoacoustic contrast agent according to an embodiment, absorption of the contrast agent into tissues may be delayed, and thus photoacoustic signals may continuously occur regardless of whether the number of blood vessels in the tissues is high or low, Therefore, the mixed contrast agent according to an embodiment may be useful in confirming a location of lesion that may be present or that may have been present in a superficial region or a deep region by photoacoustic imaging even when the lesion is reduced due to the treatment since the mixed contrast agent exists in the lesion during a period of anti-cancer treatment of breast cancer or liver cancer, According to one or more exemplary embodiment, a contrast composition may have biocompatibility and durability in the body and thus has an effect of enabling diagnosing, tracking, and observing of a location of lesions in a safe manner for a long period of time.

It should be understood that exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope of the inventive concept as defined by the following claims.

What is claimed is:

1. A method of photoacoustic imaging, the method comprising:
   administering a contrast composition for photoacoustic imaging comprising a photoacoustic contrast agent and a gelling agent to a site of a subject, wherein the photoacoustic contrast agent is charcoal and wherein the gelling agent is pectin or amylo pectin;
   between one and four weeks after administering the contrast composition including charcoal, and pectin or amylo pectin, irradiating light to the site of the subject where the contrast composition for photoacoustic imaging is administered to cause the administered charcoal to generate acoustic waves; and
   when the light is irradiated between one and four weeks after administering the contrast composition including charcoal, and pectin or amylo pectin, detecting the acoustic waves in a range of 1 MHz to 40 MHz generated by the administered charcoal to form an image.

2. The method of claim 1, wherein an amount of the photoacoustic contrast agent comprised in the contrast composition is in a range of about 0.5 (w/v) % to about 15 (w/v) %.

3. The method of claim 1, wherein an amount of the gelling agent comprised in the contrast composition is in a range of about 0.5 (w/v) % to about 15 (w/v) %.

4. The method of claim 1, wherein a wavelength of the irradiated light is in a range of about 500 nm to 1,300 nm.

5. The method of claim 1, wherein a viscosity of the gelling agent is about 50 cP to 300 cP.

6. The method of claim 1, wherein the site of the subject is at least one of a region where a lesion is present, an abdominal cavity, a heart, a gastrointestinal tract, a pancreas, a gall bladder, a spleen, lymph nodes, a liver, a kidney, or an eye.

7. The method of claim 1, wherein the contrast composition is administered in tissue or blood vessels of the subject.

8. The method of claim 1, the contrast composition having higher durability in the site of the subject compared to a contrast composition comprising charcoal alone.

* * * * *